(12) United States Patent
Whiting et al.

(10) Patent No.: US 10,253,927 B2
(45) Date of Patent: Apr. 9, 2019

(54) HEALTH METER FOR FLUIDS

(71) Applicants: Paul Whiting, Aberdeen (GB);
Andreas Nagel, Aberdeen (GB)

(72) Inventors: Paul Whiting, Aberdeen (GB);
Andreas Nagel, Aberdeen (GB)

( * ) Notice: Subject to any disclaimer, the term of this patent is extended or adjusted under 35 U.S.C. 154(b) by 0 days.

(21) Appl. No.: 15/980,563

(22) Filed: May 15, 2018

(65) Prior Publication Data
US 2018/0347751 A1   Dec. 6, 2018

Related U.S. Application Data

(63) Continuation-in-part of application No. 15/611,460, filed on Jun. 1, 2017.

(51) Int. Cl.
*F16N 29/00* (2006.01)
*F16N 39/06* (2006.01)
*G01N 27/10* (2006.01)

(52) U.S. Cl.
CPC ............ *F16N 29/00* (2013.01); *F16N 39/06* (2013.01); *G01N 27/10* (2013.01); *F16N 2200/04* (2013.01); *F16N 2210/02* (2013.01); *F16N 2210/12* (2013.01); *F16N 2250/40* (2013.01); *F16N 2260/18* (2013.01); *F16N 2270/50* (2013.01)

(58) Field of Classification Search
CPC .... B01D 2201/02; B01D 27/02; B01D 27/00; B01D 27/005; B01D 27/103; B01D 27/148; B01D 29/15; B01D 29/23; B01D 29/58; B01D 2275/201; B01D 2279/60; B01D 25/001; B01D 25/24; B01D 27/06; B01D 27/07; B01D 39/04; B01D 39/18; B01D 46/0001; B01D 46/0043; B01D 46/10; B01D 46/527; B01D 29/055; B01D 29/96; Y10S 55/05

See application file for complete search history.

(56) References Cited

U.S. PATENT DOCUMENTS

| | | | | |
|---|---|---|---|---|
| 4,855,041 A | * | 8/1989 | Church | B01D 17/0214 210/120 |
| 5,484,523 A | * | 1/1996 | Bjornsson | B01D 29/072 210/130 |
| 5,770,065 A | * | 6/1998 | Popoff | B01D 27/07 210/232 |

(Continued)

*Primary Examiner* — Randy W Gibson
*Assistant Examiner* — Gedeon M Kidanu
(74) *Attorney, Agent, or Firm* — Buskop Law Group, P.C.; Wendy Buskop (57) ABSTRACT

A health meter has a decontamination device for dirty fluid with a metal casing with metal lid, inlet port and outlet port, an open bucket having a docking lid and a plurality of openings, a hollow tube with an opening, a central hollow rod with rod opening connected to an outlet port, a convex reinforcing spacer in the open bucket, a compressible decontamination media and a reinforcing seat in the open bucket. Dirty fluid flows into the metal casing between the open bucket and metal casing through openings in the docking lid into the compressible decontamination media sequentially into the hollow tube and then into the central hollow rod and out the outlet port while an outlet sensor and an inlet sensor communicate with a controller in communication with a network and a plurality of client devices for automatic remote monitoring.

9 Claims, 10 Drawing Sheets

(56) References Cited

U.S. PATENT DOCUMENTS

| | | | | |
|---|---|---|---|---|
| 6,113,781 | A * | 9/2000 | Popoff | B01D 27/07 |
| | | | | 210/234 |
| 6,142,179 | A * | 11/2000 | Bjornsson | B60K 15/03 |
| | | | | 123/514 |
| 6,488,845 | B1 * | 12/2002 | Neufeld | B01D 29/21 |
| | | | | 210/232 |
| 6,652,740 | B2 * | 11/2003 | Schoess | B01D 27/101 |
| | | | | 210/440 |
| 2003/0015465 | A1 * | 1/2003 | Fick | B01D 29/111 |
| | | | | 210/234 |
| 2003/0178354 | A1 * | 9/2003 | Wall | B01D 29/21 |
| | | | | 210/232 |
| 2003/0226790 | A1 * | 12/2003 | Brown | B01D 29/96 |
| | | | | 210/90 |
| 2004/0011733 | A1 * | 1/2004 | Bjornsson | B01D 29/96 |
| | | | | 210/497.3 |
| 2006/0102533 | A1 * | 5/2006 | Faria | B01D 29/15 |
| | | | | 210/130 |
| 2012/0103910 | A1 * | 5/2012 | Ferrari | B01D 17/0202 |
| | | | | 210/669 |
| 2015/0014256 | A1 * | 1/2015 | Koreis | B01D 35/30 |
| | | | | 210/767 |
| 2015/0343348 | A1 * | 12/2015 | Morris | G01L 13/00 |
| | | | | 210/90 |
| 2016/0317958 | A1 * | 11/2016 | Falc'Hon | B01D 35/153 |
| 2017/0144091 | A1 * | 5/2017 | Wolhowe | B01D 36/003 |

\* cited by examiner

HEALTH METER FOR FLUIDS

CROSS-REFERENCE TO RELATED APPLICATIONS

The present application is a Continuation In Part of U.S. patent application Ser. No. 15/611,450 filed on Jun. 1, 2017 for "Health Meter for Fluids." This reference is hereby incorporated in its entirety.

FIELD

The present embodiments generally relates to a health meter for measuring decontaminated fluids, particularly transmission fluids.

BACKGROUND

A need exists for a remotely operable system that not only decontaminates fluids but also provides messaging and alarms when decontaminated fluid falls or exceeds preset limits or outside defined parameters.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways and utilized or applied in various ways.

Specific structural and functional details disclosed herein are not to be interpreted as limiting, but merely as a basis of the claims and as a representative basis for teaching persons having ordinary skill in the art to variously employ the present invention.

The invention is for a health meter having a decontamination device for dirty fluid with a metal casing with metal lid, inlet port and outlet port; an open bucket having a docking lid and a plurality of openings, a hollow tube with an opening, a central hollow rod with rod opening connected to an outlet port; a convex reinforcing spacer in the open bucket, a compressible decontamination media and a reinforcing seat in the open bucket.

The health meter enables dirty fluid to flow into the metal casing between the open bucket and metal lid through openings in the docking lid into first compressible decontamination media sequentially into the hollow tube and then into the central hollow rod and out the outlet port.

An outlet sensor and an inlet sensor communicate with a controller in communication with a network and a plurality of client devices for automatic remote monitoring.

The health meter can help prevent destruction of wildlife and fish when used in a marine environment.

The health meter can provide continuous decontamination of transmission fluids and provide immediate alarms and messages to the operator.

The embodiments extend equipment life by eliminating the need to service fluid for equipment, reducing the possibility of spilling oil into the environment, thereby reducing carbon footprint.

A benefit of the invention is that there is a reduction in the need to dispose of used transmission fluids by using the invention.

The embodiments provide a longer life for equipment seals and enable an operator to identify if fluid of equipment is healthy by continuously and automatically measuring fluid contaminant content. The invention improves lubrication conditions in operating equipment.

The embodiments reduce the risk of fires and explosions through proactive real time live monitoring therefore critical failure can be anticipated.

The invention with certain fluids can reduce high levels of contamination and thereby reduce the presence of static discharge within the system.

The invention relates to a health meter having a decontamination device for dirty fluid with a metal casing with metal lid in a first embodiment.

The metal lid has a triple purpose.

The metal lid prevents unauthorized persons from coming into contact with fluid contaminants which is a health and safety issue. The metal lid would have to be damaged to gain access to the metal casing. The metal lid also preserves decontamination for lab examination.

The metal lid acts as an open bucket inlet by providing the metal lid with cutouts that allow the fluid to pass from the metal casing into the open bucket and onto the compressible decontamination media contained in the open bucket.

The metal casing with metal lid has an inlet port and an outlet port.

The invention includes an open bucket having a docking lid.

The docking lid has a plurality of vents. Some vents have two openings.

The open bucket has a hollow tube with an opening.

The hollow tube is centrally positioned in the bucket and the central hollow rod has rod openings. The central hollow rod is connected to the outlet port of the open bucket.

The invention has a convex reinforcing spacer.

A compressible decontamination media is contained between the convex reinforced spacer and the docking lid.

The open bucket contains a reinforcing seat on which rests the convex reinforcing spacer.

In embodiments, dirty fluid flows into the health meter between the open bucket and the metal casing with metal lid.

Dirty liquid then flows though the plurality of openings of the docking lid into the open bucket and through the compressible decontamination media then sequentially into the hollow tube and then into the central hollow rod and out the outlet of the open bucket and the metal casing.

In embodiments, an outlet sensor is positioned in the outlet port and an inlet sensor is positioned in the first inlet port. A controller in communication with a network and a plurality of client devices communicates with both the inlet and outlet sensor and provides information on fluid flow and contaminant levels and decontaminated fluid leaves the decontamination device.

The controller has a processor and a computer readable media, which is non-evanescent.

The computer readable media contains instructions to instruct the processor to: (i) measure fluid flow through the inlet port; (ii) compare fluid flow through the inlet port to fluid flow through the outlet port and (iii) provide a stored message to a plurality of client devices simultaneously when fluid flow falls below stored flow limits while simultaneously (iv) measure contaminant flowing through the outlet port, (v) compare measured contaminant to stored contaminant concentrations, and (vi) generate a stored alarm to the plurality of client devices simultaneously, when the measured contaminant exceeds stored contaminant concentration.

In another embodiment, the health meter for dirty fluid has a different type of decontamination device.

In this embodiment, the decontamination device has a metal lid and a metal casing in a leak-proof engagement with the metal lid.

The metal casing has a first inlet port for receiving a dirty fluid and an outlet port for emitting a decontaminated fluid.

In this embodiment, the metal casing with metal lid contains both a first open bucket with an open bucket outlet removably contained within the metal casing and the metal lid, and a second open bucket with a second open bucket outlet removably contained within the metal casing and the metal lid stacked in alignment with the first open bucket.

In this configuration, each open bucket has a docking lid with a plurality of openings such as vents.

Each open bucket has a hollow tube with a plurality of openings.

Each open bucket of this embodiment has a convex reinforcing, spacer disposed around the hollow tube in the open bucket opposite the docking lid.

In embodiments, each open bucket contains a compressible decontamination media between the docking lid and the convex reinforcing spacer.

Each bucket has a reinforcing seat engaging around the hollow tube.

In this embodiment, the convex reinforcing spacer fits within the reinforcing seat while supporting the compressible decontamination media in each open bucket.

Dirty fluid flows into the health meter between the open buckets and the metal casing with metal lid simultaneously, and into the compressible decontamination media simultaneously.

The pair of hollow tubes each engage a central hollow rod that enables fluid flow to the outlet ports.

In this embodiment, the plurality of open buckets are contained in a single metal casing with metal lid.

This version of the health meter also has an outlet sensor positioned proximate to the outlet port and an inlet sensor positioned proximate to the inlet port. This version of the health meter also uses a controller in communication with a network and a plurality of client device. The controller also communicates to the outlet sensor and the inlet sensor.

The controller of this health meter has a processor which can be a computer, and computer readable media which can be non-transitory memory of the computer. In the computer readable media ate instructions to instruct the processor to: (i) measure fluid flow through the inlet port; (ii) compare fluid flow through the inlet port to fluid flow through the outlet port, and (iii) provide a stored message to a plurality of client devices simultaneously when fluid flow falls below stored flow limits and simultaneously (iv) measure contaminant flowing through the outlet port, (v) compare measured contaminant to stored contaminant concentrations, and (vi) generate a stored alarm to the plurality of client devices simultaneously when the measured contaminant exceeds stored contaminant concentration.

The invention also relates to a decontamination device for dirty fluid that has a metal lid. The decontamination device has a metal casing engaging the metal lid in a leak-proof engagement.

The metal casing of the decontamination device can be threaded to the lid.

The metal casing can include a first inlet port for receiving a dirty fluid; an outlet port for emitting a decontaminated fluid. In embodiments, a plurality of inlet ports can be used, as well as a sample port for sampling the contents of the decontamination device.

Inside the metal casing and metal lid there is a removable, replaceable open bucket.

The open bucket has an open bucket outlet.

A docking lid secures to the open bucket. The docking lid has a plurality of openings, which are also referred to herein as "vents".

In the open bucket, which can be a plastic, is installed a hollow tube with a plurality of openings.

Inside the hollow tube is installed a central hollow rod with a rod opening.

The central hollow rod is in fluid communication with the outlet port.

A convex reinforcing spacer is disposed around the hollow tube in the open bucket opposite the docking lid.

A compressible decontamination media such as wrapped cellulose sheet, can be contained between the docking lid and the convex reinforcing spacer.

The open bucket can have a reinforcing seat that in embodiments may be built into the wall of the open bucket, interior of the bucket for receiving the convex reinforcing spacer while supporting the compressible decontamination media in the open bucket.

For the decontamination device, the dirty fluid flows into the decontamination device between the open bucket with attached docking lid and the metal casing with metal lid, through the openings or vents of the docking lid into the compressible decontamination media, then the fluid sequentially continues to flow into the hollow tube and then into the central hollow rod and out the outlet port.

In an embodiment of decontamination device a plurality of open buckets with docking lids can be stacked in a single metal casing with lid for simultaneous processing of dirty fluid.

The following terms are used herein:

The term "compressible decontamination media" can refer to cellulose media. The compressible media can be a recycled material with a porosity enabling a fluid flow of dirty fluid, such as transmission fluid, water, or glycol, at a rate of 0.5 to 3 liters per minute per open bucket. In embodiments, the compressible material can be a rolled material, made from cellulose fibers or similar fibrous material. In embodiments, the compressible material can be paper.

The term "convex reinforcing spacer" refers to a device with a plurality of ribs. The convex reinforcing spacer can have a diameter from 150 to 190 millimeters. Each spacer can have in cross section ribs that are tapered at an angle between 15 and 18 degrees. Each spacer can have an outer ring with 10 to 16 attached ribs around a hollow center that clips into the hollow tube. Clips can be used projecting from the hollow center to engage the hollow tube. The clips keep the convex reinforcing spacer a distance from the hollow tube. The convex reinforcing spacer can have a corrugated edge on each of the attached spokes to allow the decontaminated fluid to flow between spokes for higher flow rates.

The term "docking lid" refers to the lid that is installed over the open bucket and contained within the metal casing with metal lid. The docking lid enables a second open bucket to be stacked on the docking lid of a first open bucket for simultaneous processing of dirty fluid. The docking lids have openings which are defined herein. The docking lids not only provide openings but also provide load support as the open buckets become heavier with dirty liquid.

The term "metal lid" refers to a thin lid that can be metal that engages with the metal casing by using fasteners. The metal lid in embodiments can have a thickness of between 1 to 2 millimeters. The metal lid can be flat or sloped. The metal lid can have a diameter between 100 millimeters and 240 millimeters. The metal lid can be sloped at an angle between 5 and 30 degrees. In embodiments, the metal lid is made from stainless steel.

The term "reinforcing seat" refers to a material that can be integral with the open bucket. The reinforcing seat has a lip that provides reinforcement keeping the seat self-centering in the open bucket. The reinforcing seat can be made from the same material as the open bucket. Other materials may be bonded to the reinforcing seat.

The term "openings" refers to a plurality of individual slits or cutouts formed in the docking lid. The opening in embodiments can be a double opening. The openings can have a variety of shapes, such as triangular shaped openings. The openings can vary in size. The openings can have opening dimensions with widths ranging from 2 to 8 millimeters. In embodiments, the openings can vary in size around the docking lid. Between 2 and 30 openings can be used in each docking lid. In embodiments, the opening can he oriented concentrically around the hollow tube.

EXAMPLE

The embodiments can operate as a health meter for gear boxes or turbines or other hydraulic systems such as compressors.

The embodiments can attach to a lubrication reservoir of a turbine.

In embodiments, a decontamination device receives dirty fluid that is dirty lube oil or control fluid which would have could contain a contaminate, such as water, or acid, or varnish.

The decontamination device of this example can have a stainless steel metal lid that attaches to a stainless steel metal casing. In this example, the metal lid can be 212 millimeters in diameter. The metal casing can have a volume of approximately 6 liters. The metal lid of this example attaches to the metal casing with a threaded engagement and is centrally oriented over a hollow rod and secured with a nut.

As an example, the metal casing can have a first inlet port that is 13.3 millimeters in diameter for receiving dirty fluid at a flow rate of one liter per minute per compressible decontamination media used in an open bucket.

As an example, the outlet port can have the same dimensions as the inlet port. The outlet port allows decontaminated fluid toy flow out the metal casing.

As an example, the invention can use four open buckets stacked on top of each other via the docking lids, all contained in one metal casing secured with one metal lid.

In this example, the four open buckets can be used in parallel to decontaminate fluid simultaneously.

Each of the open buckets can have a compressed decontaminate material.

In an embodiment, the compressed decontaminate material can be identical.

In other embodiments, the compressed decontaminate material can differ from open bucket to open bucket.

In embodiments, open buckets can have a dimension ranging from 50 to 200 centimeters high by 12 to 60 centimeters wide, such as one meter by 0.6 meters.

The material of the open bucket can he made from a plastic, or a reinforced plastic, and may be made from crystalline polypropylene homopolymer that may include additional additives, such as antioxidant corrosion inhibiting stabilizers.

In this example, the open bucket can have an open bucket outlet to flow out cleaned fluid.

As an example, the docking lid can be made from the same material as the open bucket.

The docking lid for use in treating transmission fluid from a turbine engine, the docking lid can have 28 openings (or vents). Each opening can be positioned equidistantly around a center in the docking lid. Each opening can have a dimension that is triangular such as, a 13 square millimeter opening.

A hollow tithe can be used in the open bucket that can be 200 millimeters long with an opening at the lower center of the hollow tube. The opening can be 26.2 millimeters in diameter. The hollow tube can he made from cardboard.

A central hollow rod can be inserted in the hollow tube.

The central hollow rod has an opening to receive fluid from the compressed decontamination media.

The central hollow rod in this example, engages each of the four compressed decontamination medias (or materials).

The central hollow rod can have an overall length of 1076 millimeters. The diameter of the central hollow rod can be 21 millimeters.

The central hollow rod has a rod opening at the upper end of the central hollow rod adjacent but below the docking lid.

In embodiments, an additional hole can be formed in the central hollow rod, such as at a second location 30 millimeters below the top of the hollow rod.

The hollow tube flows decontaminated fluid, that is, "cleaned fluid" to the outlet port.

In this example, four convex reinforcing spacers are used, one in each open bucket.

In this example, the four compressible decontamination medias can be identical, such as a roll of one continuous sheet of recycled paper wherein the sheet is 0.001 centimeters thick and each sheet is as tall as the open bucket is tall, and up to 10% less in height.

Each compressible decontamination media is contained between the docking lid and the convex reinforcing spacer. The continuous sheet can be 260 meters in length wound around the hollow tube.

In other embodiments, the compressible decontamination media can be made from different materials, that is, one open bucket can have one material, while a second open bucket has a different compressible decontamination material. In another embodiment, the compressible decontamination media can be made from a first spongy cellulose on the outside (a first material) and a different type of contaminant absorber (a second material) mount around the hollow tube. That is, the spongy cellulose is wound around the second material.

In this embodiment, the convex reinforcing spacers are formed to be integral and as a part of each open bucket. The convex reinforcing spacers can be made from hard plastic with rounded beveled edges engaging the compressible decontamination material, and specifically excluding a knife like edge. The embodiments provide a safer environment because the reinforcing spacers do not sharp edges.

Four reinforcing seats are used in this example. Each reinforcing seat engages around one of the hollow tubes.

Each convex reinforcing spacer is within a reinforcing seat without clipping and each convex reinforcing spacer supports the compressible decontamination media in the open bucket.

In embodiments, the metal casing is threaded closed with the metal lid and simultaneously, the open bucket is closed with the docking lid.

The dirty fluid flows through the plurality of openings in the docking lid simultaneously, into and through compressible decontamination media and then into the hollow tube.

The decontaminated fluid flows from the hollow tube into the central hollow rod and out the outlet port.

In this example, fluid pressure in the metal casing with metal lid is maintained at about 2.5 bar. As the metal casing heats up, the metal casing expands slightly and then as the metal casing cools, the metal casing returns to its original shape.

In other embodiments, the dirty fluid can be processed at gravimetric pressure.

As an example, an outlet sensor can be used to detect contaminants such as 10 ppm water, particulates, and/or varnish by the outlet sensor positioned in or proximate to the outlet port.

An inlet sensor positioned in or proximate to an inlet port can provide a delta of contaminant percentage change between inlets and outlet.

A controller for the health meter can be a programmable logic circuit with associated memory, which is "computer readable media" that is non-evanescent.

In an example, when the controller is a computer, the controller can be in wired or wireless communication with a global communication network.

The global communication network can be a cellular network, a satellite network, a local area network, a wide area network, and combinations thereof.

The controller is in wired or wireless communication with each of the inlet sensors and the outlet sensor.

The controller can have a processor made by Raspberry Pic™ or Intel™ and computer readable media.

In an embodiment, the processor can be a cloud based processor.

Computer readable media can be a memory area, a jump drive, a hard drive or a cloud based memory area.

The computer readable media can contain instructions to instruct the processor to measure fluid flow through the inlet port or plurality of inlet ports.

The computer readable media can contain instructions to instruct the processor to compare measured fluid flow through the outlet port.

The computer readable media can contain instructions to instruct the processor to provide a stored message to a plurality of client devices simultaneously when fluid flow falls below stored flow limits.

The stored messages are in the computer readable media, such as the message: "check inlet port" when the compared flow rate is 10% less than stored flow limits for this transmission fluid.

The stored flow limits can be a rate of flow through the inlet port by type of fluid, such as 10% water in hydraulic oil at two liters per minute.

The computer readable media can contain instructions to instruct the processor to measure contaminant through the outlet port, such as measure glycol content in the fluid by concentration.

The computer readable media can contain instructions to instruct the processor to compared measured contaminant to stored contaminant concentrations.

Examples of stored contaminant concentrations can be 0.1 to 0.001% glycol in hydraulic fluid, which is acceptable at a flow rate of one liter per minute.

The computer readable media can contain instructions to instruct the processor to generate a stored alarm to the plurality of client devices simultaneously when the measured contaminant exceeds stored contaminate concentration.

The computer readable media containing the stored contaminant concentrations can be a range of concentrations for a range of transmission fluids.

The stored alarms could be text alarms such as the message: "urgent—act now—contaminant issue" accompanied by buzzing, beeping or a big question mark as a visual indicator.

The client device can be cell phones, laptops, tablets, personal computers, wearable computers, or similar communication and processing devices capable of bidirectional communication.

For example, if the contaminant is water, and the outlet sensor detects water as the decontaminated fluid. The decontaminated fluid exits the outlet port. Then the instruction in the computer readable media compares the measured contaminant to contaminant concentrations stored in the computer readable media. The instructions generate and transmit an alarm to three operator cell phones when the measured contaminant exceeds the stored contaminant concentration for the transmission fluid, such as 200 ppm of water, or exceeds a stored contaminant differential such as 2% in particulate count for particles having a diameter over four micron.

The invention also relates to a decontamination device having the parts listed above.

In embodiments, the health meter can have electrodes in the outlet port and one or more of the inlet ports. The electrodes are in communication with the controller.

If electrodes are used, the computer readable media would also contain instructions to instruct the processor to compare electrode measurements for conductivity at the inlet port to the outlet port.

In embodiments, the health meter can have a second inlet port in the metal casing enabling parallel connection of multiple health meters for parallel processing.

In embodiments, the health meter metal easing and docking lid are steel or a non-deforming plastic capable of sustaining pressures from one bar to up to six bar without deforming.

In embodiments, the docking lid has a sampling port.

In embodiments, the health meter has an open bucket, convex reinforcing spacer and reinforcing seat all made from a flexible material comprising a polymer selected from the group: polyethylene polyketone (PEEK), homopolymers of polyethylene, homopolymers of polypropylene, polyvinyl chloride and copolymers thereof.

In embodiments, the open bucket is a flexible open bucket.

In embodiments, the health meter uses a hollow tube made from one or more of the following: cardboard, a flexible metal, and a flexible material containing a polymer selected from the group: polyethylene polyketone (PEEK), homopolymers of polyethylene, homopolymers of polypropylene, polyvinyl chloride and copolymers thereof.

In embodiments, the health meter has a reinforcing seat that is integral with the open bucket positioned at the bottom of the open bucket.

In embodiments, the health meter has a convex reinforcing spacer that is integral with the open bucket and positioned proximate to the bottom of the open bucket.

In embodiments, the convex reinforcing spacer is positioned around the hollow tube in the reinforcing seat.

In embodiments, the convex reinforcing spacer is a disc shape.

In embodiments, the health meter processes as the dirty fluid, a transmission fluid.

In embodiments, the health meter has a compressible straining mesh mounted between the convex reinforcing spacer and the open bucket around the hollow tube.

In embodiments, the health meter operates at temperatures from −20 degrees Celsius to +120 degrees Celsius without dogging, without reducing flow rates and without deforming given physical parameters of the dirty fluid.

In an embodiment, the convex reinforcing spacer is integral with the open bucket and positioned proximate to a bottom of the open bucket.

Figure 1:
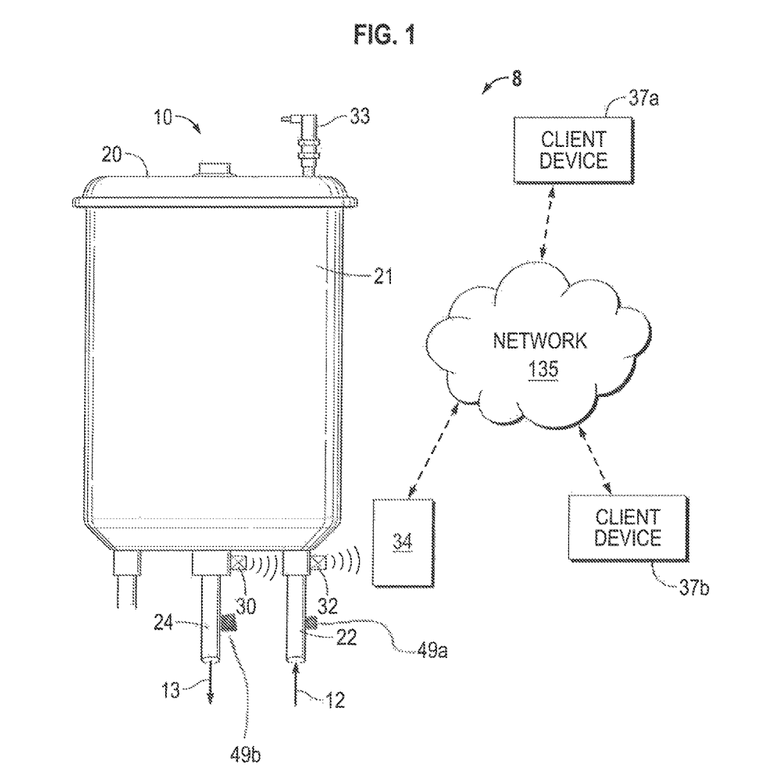
FIG. 1 depicts a diagram of the health meter according to one or more embodiments.

Turning now to the Figures, FIG. 1 shows the health meter 8 for dirty fluid 12.

The health meter 8 has a decontamination device 10.

The decontamination device 10 has a metal lid 20 engaging a metal casing 21 in a leak-proof engagement.

The metal casing 21 has a first inlet port 22 for receiving a dirty fluid 12 and an outlet port 24 for emitting a decontaminated fluid 13.

In embodiments, an outlet sensor 30 is positioned in or proximate to the outlet port 24 and can be wirelessly connected to or connected in a wired engagement to a controller 34 that is remote to the metal casing 21.

An inlet sensor 32 is positioned in or proximate to the inlet port 22 and can be wirelessly connected to or connected in a wired engagement to a controller 34 that is remote to the metal casing 21.

The controller 34 can be in communication with a network 135 and a plurality of client devices 37a and 37b that communicate with the network.

In this Figure the metal lid 20 has a sampling port. In embodiments electrodes 49a and 49b are connected to one of the inlet ports receiving dirty fluid 12a or 12b and the outlet port 24 emitting decontaminated fluid 13.

Figure 2A:
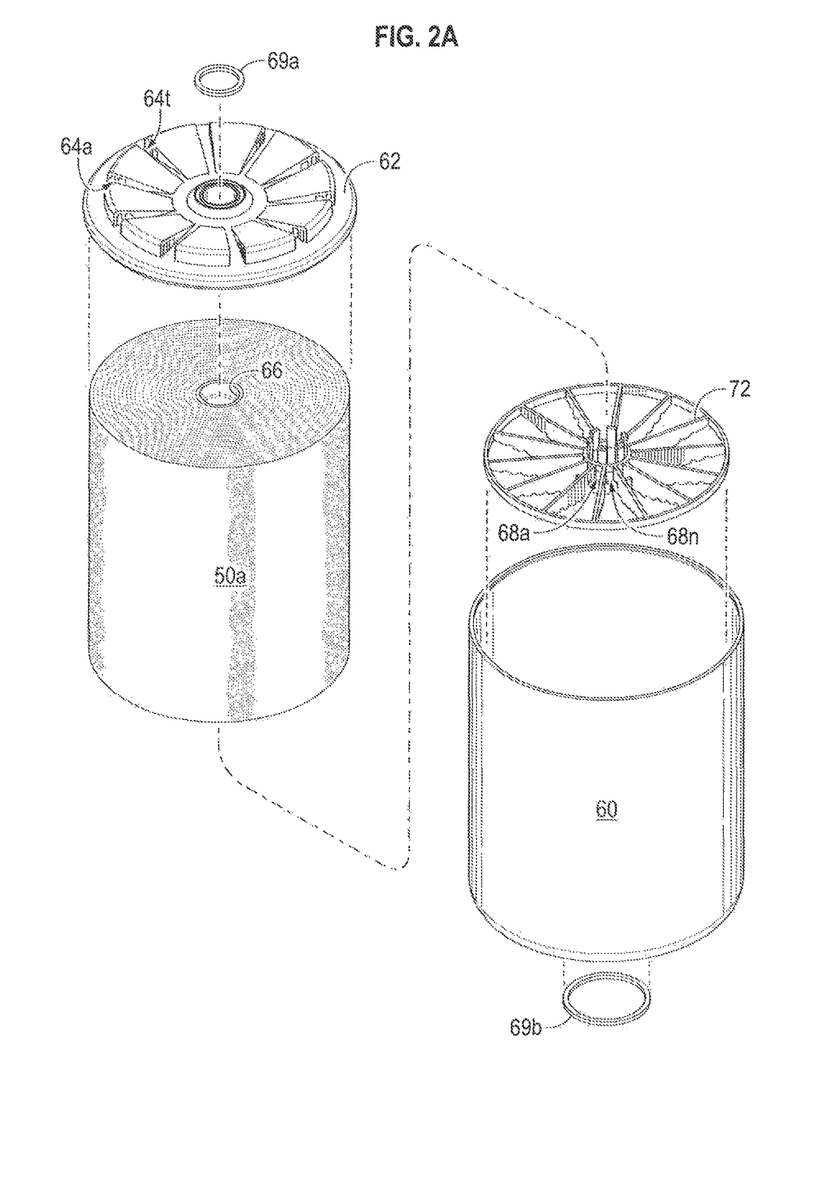
FIGS. 2A and 2B depicts exploded views of the open bucket with docking, lid according to one or more embodiments.
Figure 2B:
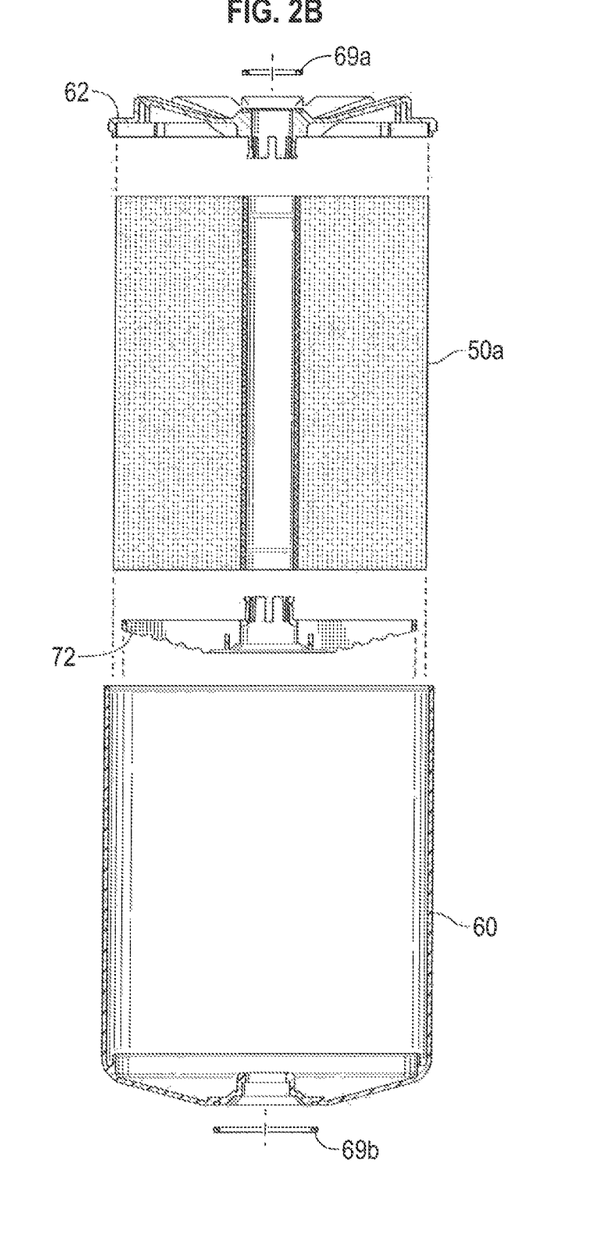

FIGS. 2A and 2B are a perspective exploded view of a portion of the health meter showing an open bucket 60 with docking lid 62.

The open bucket 60 is removably contained within the metal casing and metal lid.

The open bucket has a docking lid 62 with a plurality of vents (which are openings) 64a to 64t.

The open bucket 60 has a convex reinforcing spacer 72 disposed around a hollow tube 66 in the open bucket 60.

The convex reinforcing spacer 72 has a plurality of openings 68a to 68n allowing fluid to flow through the openings.

A compressible decontamination media 50a is contained between the docking lid 62 and the convex reinforcing spacer 72. Additional rings 69a and 69b can be used to fasten components together.

Figure 3:
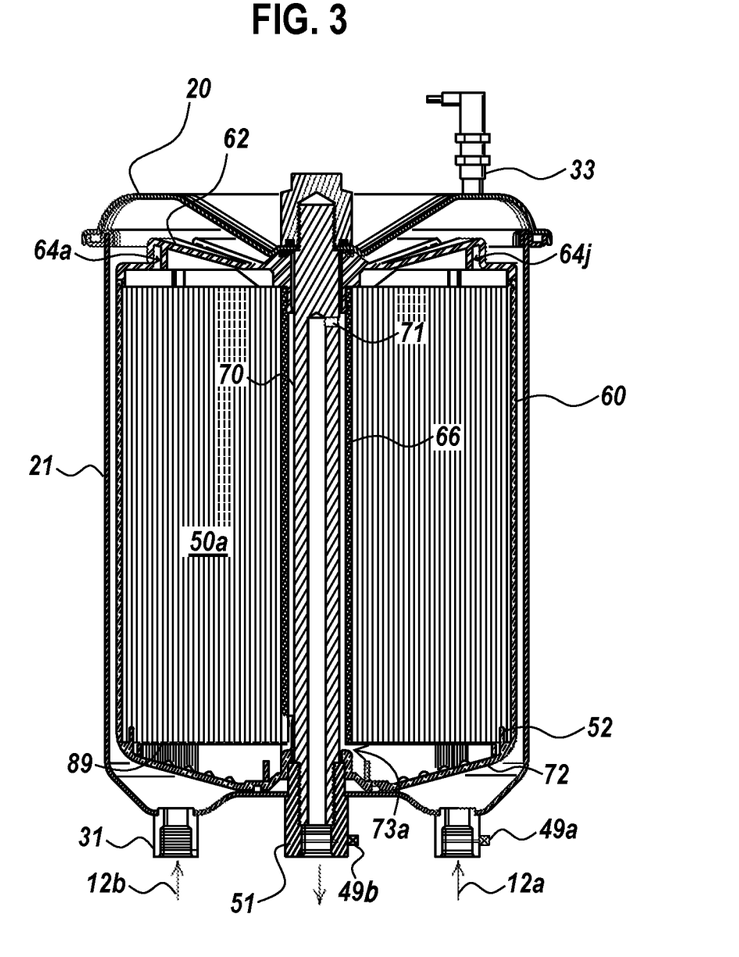
FIG. 3 depicts a cross sectional view of an open bucket with docking lid according to one or more embodiments.

FIG. 3 is a cross sectional view of an open bucket 60 with an open bucket outlet within the metal casing 21. Decontaminated fluid 13 flows from the open bucket outlet.

A hollow tube 66 is shown, which has a hollow tube opening 73a. More openings are shown in other Figures.

In embodiments, a central hollow rod 70 with a rod opening 71 is contained within the hollow tube in fluid communication with the open bucket outlet.

A convex reinforcing spacer 72 is disposed around the hollow tube 66 in the open bucket 60 opposite the metal lid 20.

A compressible decontamination media 50a is contained between the metal lid 20 and the convex reinforcing spacer 72.

A reinforcing seat 52 without a knife edge engages around the hollow tube 66. This configuration provides a safer device to human and operator use preventing cutting off portions of hands and fingers.

The convex reinforcing spacer 72 fits within the reinforcing seat 52 while the convex reinforcing spacer 72 supports the compressible decontamination media 50a in the open bucket 60.

In embodiments, a docking lid is shown with a plurality of vents 64a to 64j.

When dirty fluid flows into the metal casing with metal lid, fluid passes through the vents in the docking lid into the compressible decontamination media. Next, the fluid sequentially flows between the hollow tube 66 and the central hollow rod 70. Then, the fluid flows into the central hollow rod and out the open bucket outlet and through the outlet port.

In embodiments, the number of openings (vents) may vary.

Thicker viscosity liquid for processing may require more openings (vents) than a thinner viscosity liquid in order to flow freely.

In embodiments, a second inlet port 31 in the metal casing enables parallel connection of multiple metal casings together for parallel processing of fluid.

In embodiments, a sample port 33 is shown.

In embodiments, electrodes 49a and 49b are connected to one of the inlet ports receiving dirty fluid 12a or 12b and the outlet port 51 emitting cleaned, decontaminated fluid 13.

A compressible straining mesh 89 is shown between the convex reinforcing spacer 72 and the compressible decontamination media 50a around the hollow tube.

Figure 4:
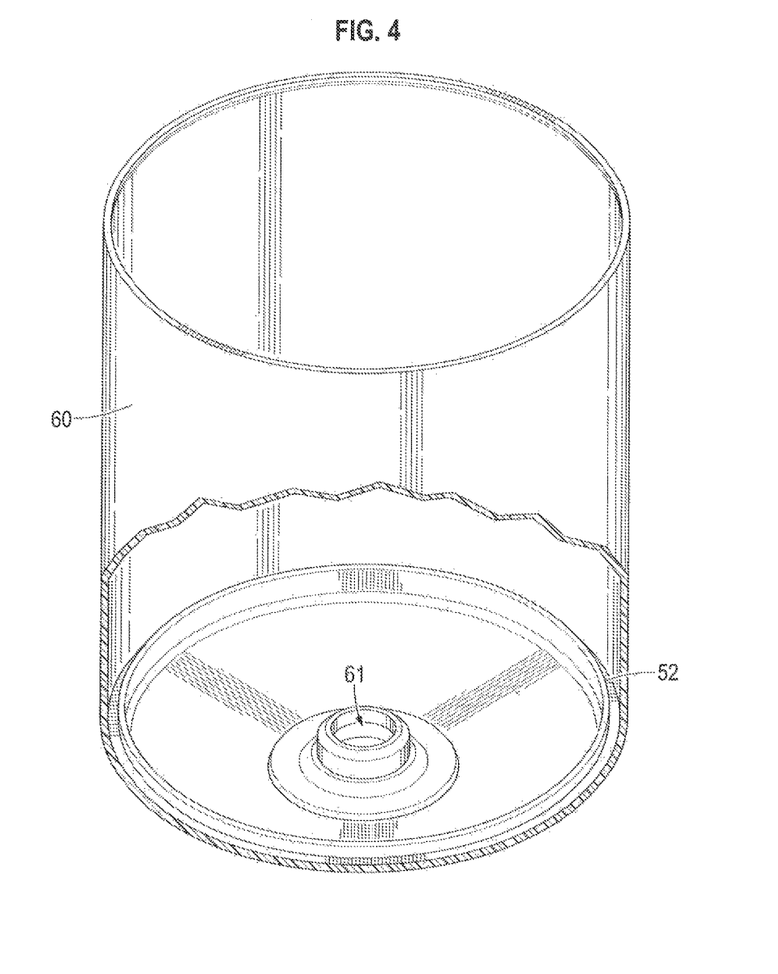
FIG. 4 depicts a cut view of an open bucket according to one or more embodiments.

FIG. 4 is a cut view of the open bucket 60 showing a reinforcing seat 52 engaging around the hollow tube.

In embodiments, the open bucket contains an open bucket outlet 61.

Figure 5:
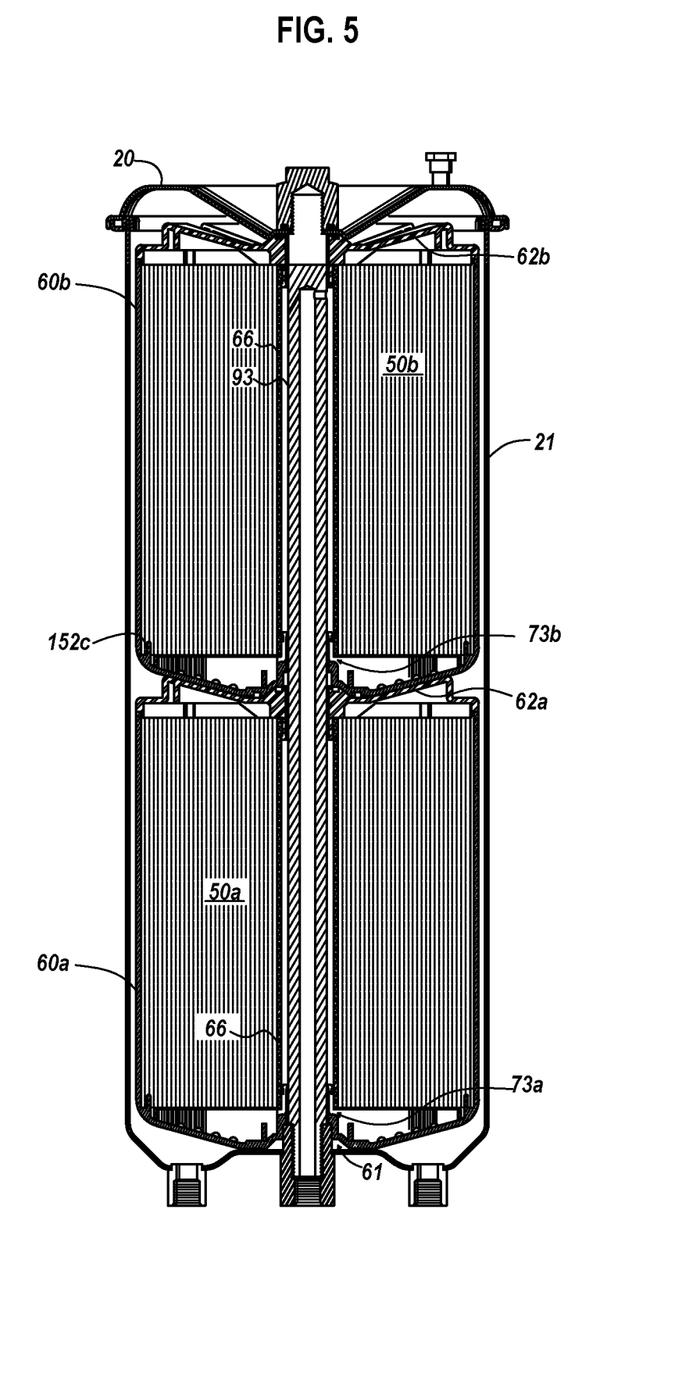
FIG. 5 depicts a two bucket arrangement according to one or more embodiments.

FIG. 5 depicts a two open bucket arrangement according to one or more embodiments.

The plurality of open buckets 60a and 60b contain a docking lid, 62a and 62b respectively.

The plurality of open buckets having a common rod 93 through each hollow tube 66 of each open bucket 60a and 60b.

In embodiments, the plurality of open buckets is contained in a single metal easing 21 with metal lid 20. Two different compressible decontamination media 50a and 50b are shown.

Figure 6:
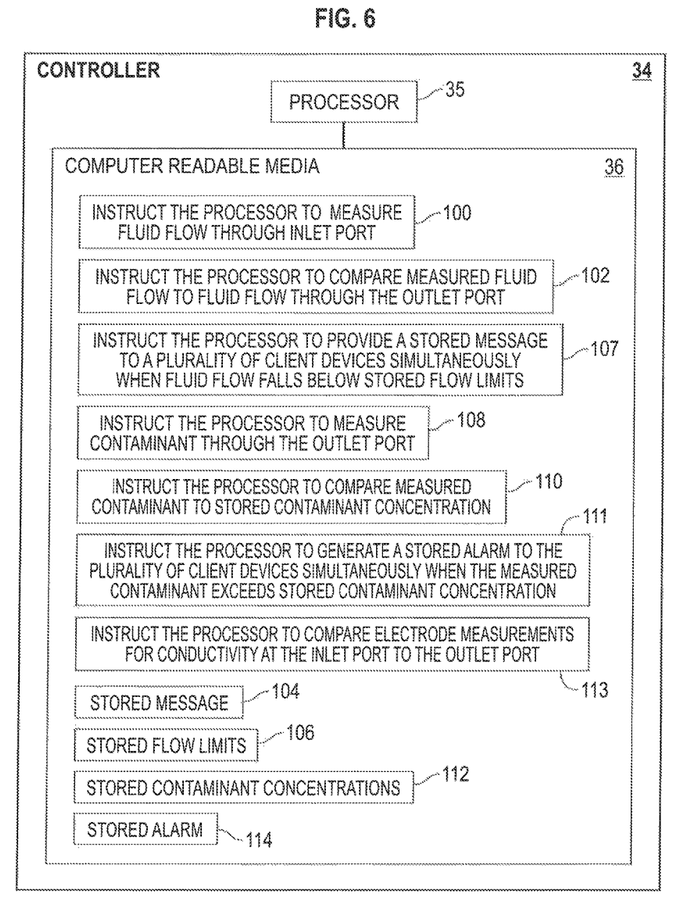
FIG. 6 depicts a diagram of the controller according to one or more embodiments.

FIG. 6 is a diagram of a controller 34 with processor 35 and computer readable media 36 usable in the invention.

The computer readable media 36 contains instructions 100 to instruct the processor to to measure fluid flow through an inlet port, such as using a conventional flow meter.

The computer readable media 36 contains instructions 102 to instruct the processor to compare measured fluid flow at the inlet port to fluid flow through the outlet port.

In embodiments, the computer readable media 36 contains stored messages 104, stored flow limits 106, stored contaminate concentrations 112, and stored alarms 114.

The computer readable media 36 contains instructions 107 to instruct the processor to provide a stored message to a plurality of client devices simultaneously when fluid flow falls below stored flow limits.

In embodiments, the controller 34 contains instructions 10$ in the computer readable media 36 to instruct the processor to measure contaminant through the outlet port.

The computer readable media 36 contains instructions 110 to instruct the processor to compare measured contaminant to stored contaminant concentration.

The computer readable media 36 contains instructions 111 to instruct the processor to generate a stored alarm to the plurality of client devices simultaneously when the measured contaminant exceeds stored contaminant concentration.

The controller contains instructions 113 in the computer readable media 36 to instruct the processor to compare electrode measurements for conductivity at the inlet port to the outlet port.

To assemble the decontamination device, the open bucket with hollow tube has compressible decontamination media installed in the open bucket.

A docking lid is installed over the open bucket.

The open bucket with docking lid is installed in the metal casing.

A metal lid is secured to the metal easing.

The docking lid enables stacking of a plurality of open buckets within a single metal casing with a single metal lid.

Figure 7A:
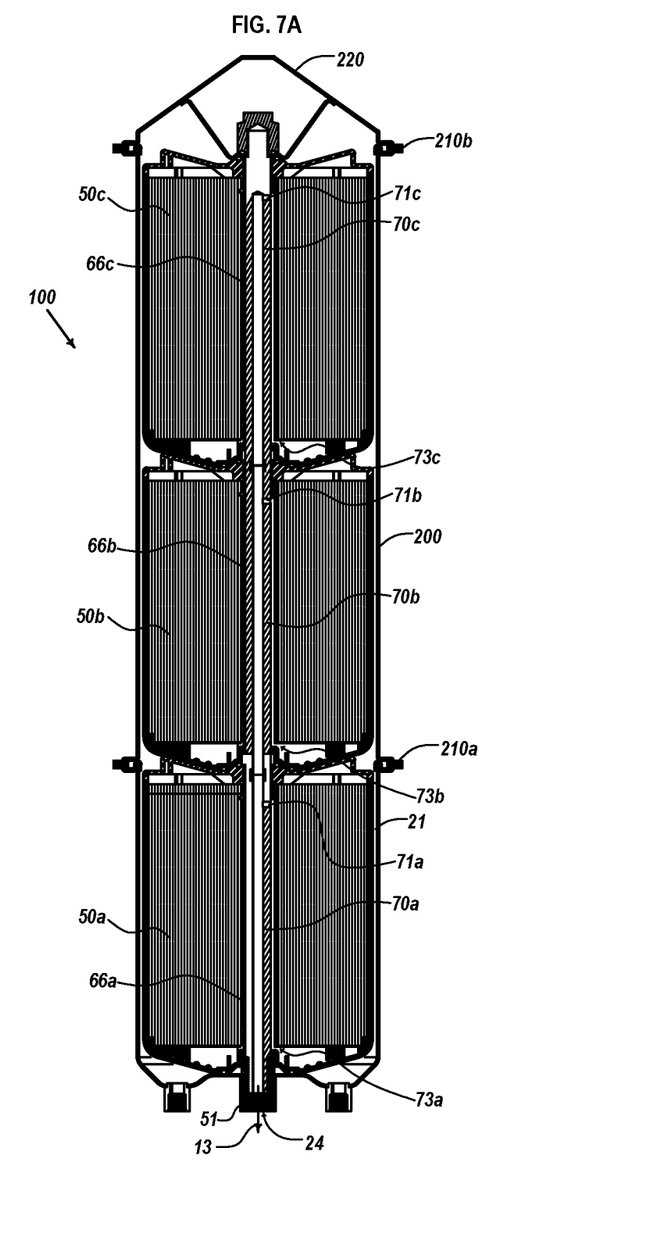
FIGS. 7A-7C depict an embodiment of the invention.
Figure 7B:
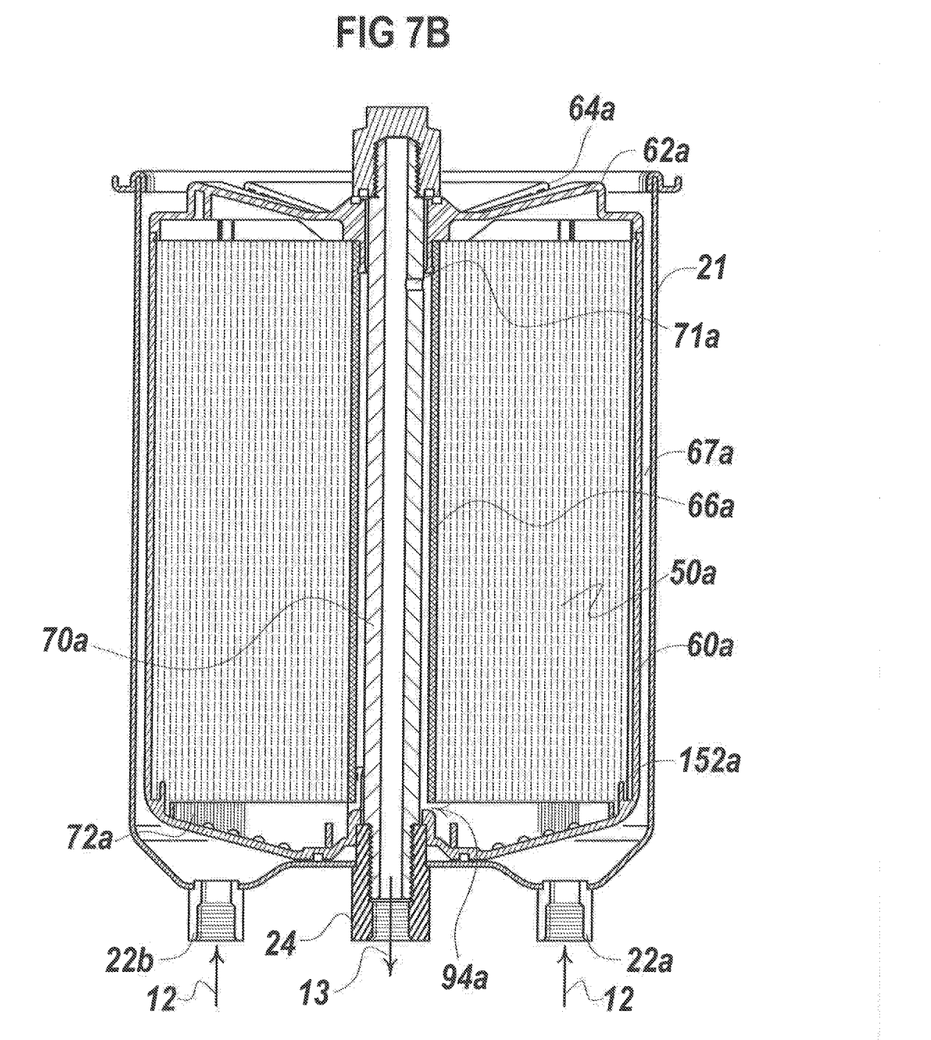
Figure 7C:
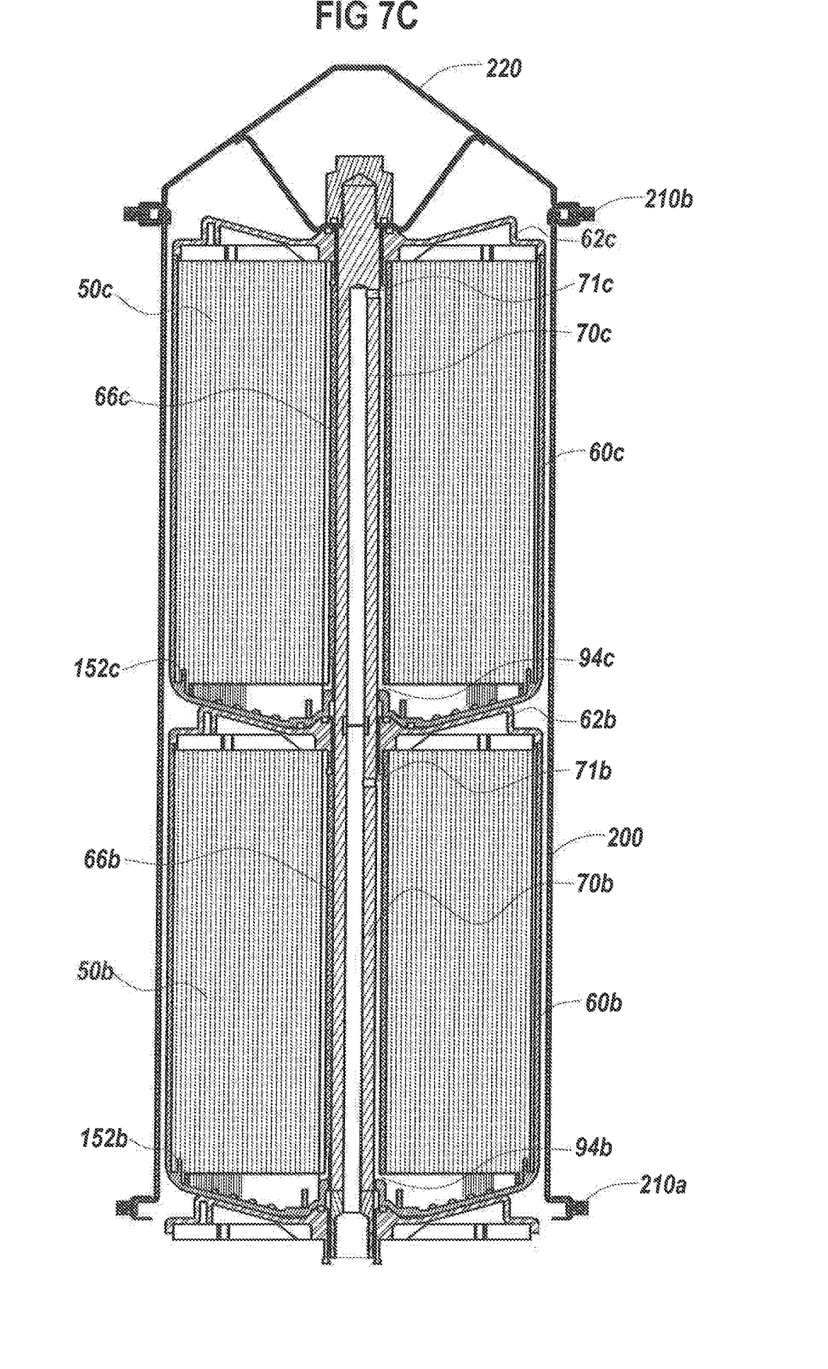

FIGS. 7A-7C depict an embodiment of the invention. FIG. 7A shows a stacked assembly.

A health meter 100 for dirty fluid is shown with three decontamination media.

The health meter has a metal casing 21 with a first inlet port 22a for receiving a dirty fluid 12 and a second inlet port 22b for receiving dirty fluid and an outlet port 24 for emitting a decontaminated fluid 13.

This two part assembly of the health meter has in the metal casing 21 with an open buckets 60a. In embodiments, the open bucket 60a has an open bucket outlet 61 (shown in FIG. 4) and an extension cylinder 200 is attached to the metal casing 21.

The open bucket 60a is removably contained within the metal casing 21.

This open bucket 60a has a docking lid 62a with a plurality of vents 64a to allow dirty fluid to enter.

The open bucket 60a has a first hollow tube 66a which can be made from cardboard.

The first hollow tube 66a has a passage 94a surrounding the first hollow tube 66a.

A first central hollow rod 70a that can be steel, has an opening 71a. The first central hollow rod 70a is in fluid communication with the outlet port 24.

Decontaminated fluid flows into the passage 94a then sequentially into the opening 71a and out the first central hollow rod 70a.

This embodiment shows a first convex reinforcing spacer 72a disposed around the hollow tribe in the open bucket opposite the docking lid.

A first compressible decontamination media 50a is contained between the docking lid 62a and the first convex reinforcing spacer 72a.

A first reinforcing seat 152a is installed in the open bucket for receiving the first convex reinforcing spacer while supporting the first compressible decontamination media in the open bucket.

Dirty fluid flows into a space 67a between the open bucket with the attached docking lid 62a and the metal casing 21 through the plurality of vents 64a into the compressible decontamination media 50a then sequentially into the first hollow tube 66a and then into the first central hollow rod 70a and out the outlet port 24 as the decontaminated fluid 13.

Attached to the metal casing is an extension cylinder 200. The extension cylinder 200 can be the same diameter as the metal casing, or a different diameter. The wall thickness of the extension cylinder should be the same as the metal casing, unless a different material is used, wherein the thickness can change.

An exemplary extension cylinder length can be 750 mm with an inner of diameter that matches the metal casing inner diameter, such as 196 mm inner diameter and a wall thickness of 1.65 mm, and wherein the extension cylinder can be made from non-deforming metal capable of sustaining pressure from 100 to 300 psi.

The extension cylinder 200 is secured to the metal casing with a first fastener 210a that can be a sealing compression clamp.

On the opposite end of the extension cylinder is a closable lid 220 that is removably secured to the extension cylinder opposite the open bucket with the second fastener 210b that can be a sealing compression clamp.

A plurality of open buckets 60b and 60c are connected in series inside the extension cylinder. Each open bucket has a docking lid 62b and 62c respectively.

A plurality of compressible decontamination media 50b, 50c are contained in each open bucket in the extension cylinder.

The extension cylinder 200 has a plurality of permeable reinforcing seats 152b and 152c extending across each open bucket. Each permeable reinforcing seat supports compressible decontamination media in the open bucket in the extension cylinder.

A plurality of hollow tubes 66b and 66c in each open bucket.

Each hollow tube fluidly separated from another hollow tube.

Each hollow tube having a passage 94b and 94c respectively. Each passage surrounds each hollow tube and enables transfer of decontaminated fluid from the compressible decontamination media to the open bucket outlet.

A plurality of threadably engagable central hollow rods 70b and 70c are contained in each open bucket 60b and 60c.

Each threadably engageable central hollow rod 70b and 70c has a rod opening 71b, 71c respectively.

Each central hollow rod is contained within each hollow tube. In embodiments, each central hollow rod is in fluid communication with the open bucket outlet.

The extension cylinder 200 is secured on the first end to the metal casing 21 containing the first open bucket 60a and the central hollow tube 66a in the open bucket threadably engages the second and third hollow tubes 66b and 66c of the open buckets 60b and 60c of the extension cylinder 200 through a center of the reinforcing seats 152b and 152c.

Dirty fluid flows into the extension cylinder 200 between the extension cylinder through a space 67a for processing through a plurality of compressible decontamination media 50a-50c then into the hollow tubes 66a-66c and then into the connected hollow rods as cleaned decontaminated fluid 13.

While these embodiments have been described with emphasis on the embodiments, it should be understood that within the scope of the appended claims, the embodiments might be practiced other than as specifically described herein.

What is claimed is:

1. A health meter for dirty fluid comprising:
   (a) a metal casing comprising;
      (i) a first inlet port for receiving a dirty fluid;
      (ii) an outlet port for emitting a decontaminated fluid;
   (b) a first open bucket with a first open bucket outlet removable contained within the metal casing, the first open bucket comprising;
      (i) a docking lid comprising a plurality of vents;
      (ii) a first hollow tube;
      (iii) a passage in the first hollow tube;
      (iv) a first central hollow rod with an opening, the first central hollow rod in fluid communication with the outlet port, wherein decontaminated fluid flows into the passage into the opening and out the first central hollow rod;
   (c) a first convex reinforcing spacer disposed around the hollow tube in the first open bucket opposite the docking lid;
   (d) a first compressible decontamination media contained between the docking lid and the first convex reinforcing spacer;
   (e) a first permeable reinforcing seat receiving the first convex reinforcing spacer and supporting the first compressible decontamination media in the open bucket, and wherein dirty fluid flows into a space between the open bucket with the attached docking lid and the metal casing then through the vents into the compressible decontamination media then sequentially into the first hollow tube and then into the first central hollow rod and out the outlet port as the decontaminated fluid;
   (f) an extension cylinder connected to the metal casing with a first fastener;
   (g) a closable lid secured removable to the extension cylinder opposite the first open bucket with a second fastener; the extension cylinder receiving dirty fluid in parallel from the inlet of the metal casing;
   (h) a plurality of open buckets connected in series in the extension cylinder, each open bucket having a docking lid;
   (i) a plurality of compressible decontamination media, one of the compressible decontamination media contained in each open bucket of the extension cylinder;
   (j) a plurality of reinforcing seats extending across each open bucket in the extension cylinder, each reinforcing seat supporting compressible decontamination media in; each open bucket;
   (k) a plurality of hollow tube, each hollow tube having a passage in the hollow tube;
   (l) a plurality of threadably engageable central hollow rods, each with a rod opening, each central hollow rod contained within each hollow tube, each central hollow rod in fluid communication with the open bucket outlet; wherein the extension cylinder is secured on the first end to the metal casing containing the first open bucket forming a stacked assembly and wherein the central hollow tube in the first open bucket threadably engages the second and third hollow tubes of the extension cylinder through a center of the reinforcing seats;
   wherein dirty fluid flows into the extension cylinder into the space between the extension cylinder and open buckets for processing by the plurality of compressible decontamination media then into the connected hollow rods as cleaned decontaminated fluid using the stacked assembly.

2. The health meter of claim 1, comprising a second inlet port in the metal casing enabling parallel connection of multiple decontamination devices for parallel processing.

3. The health meter of claim 1, wherein the metal casing and metal lid are steel or a non-deforming plastic capable of sustaining pressures from 1 bar to up to 6 bar without deforming.

4. The health meter of claim 1, wherein the metal lid has a sampling port.

5. The health meter of claim 1, wherein the open bucket, the convex reinforcing spacer and the reinforcing seat comprise a flexible material comprising a polymer selected from the group: polyethylene polyketone (PEEK), homopolymers of polyethylene, homopolymers of polypropylene, polyvinyl chloride and copolymers thereof.

6. The health meter of claim 1, wherein the hollow tube comprises: cardboard, a flexible metal, and a flexible material comprising a polymer selected from the group: polyethylene poly ketone (PEEK), homopolymers of polyethylene, homopolymers of polypropylene, polyvinyl chloride and copolymers thereof.

7. The health meter of claim 1, wherein the permeable reinforcing seats or the convex reinforcing spacer is integral with the open bucket proximate a bottom of the open bucket and has a plurality of openings.

8. The health meter of claim 1, wherein the metal casing and metal lid operate from −20 degrees Celsius to +120 degrees Celsius without clogging, without reducing flow rates, and without deforming dependent on dirty fluid physical characteristics.

9. The health meter of claim 1, comprising:
   an outlet sensor positioned proximate the outlet port for fluid flow detection;
   an inlet sensor positioned proximate the inlet port for fluid flow detection;
   electrodes connected to the inlet port and the outlet port and in communication with the processor and instructions in the computer readable media for instructing a processor of a controller to compare electrode measurements for conductivity at the inlet port to the outlet port wherein the controller is in communication with a network and a plurality of client devices the outlet sensor and the inlet sensor, the controller comprising:
   (a) the processor;
   (b) computer readable media with instructions to instruct the processor to: (i) measure fluid flow through the inlet port; (ii) compare fluid flow through the inlet port to fluid flow through the outlet port; and (iii) provide a stored message to a plurality of client devices simultaneously when fluid flow falls below stored flow limits and simultaneously (iv) measure contaminant flowing through the outlet port; (v) compare measured contaminant to stored contaminant concentrations and (vi) generate a stored alarm to the plurality of client devices simultaneously when the measured contaminant exceeds stored contaminant concentration.

* * * * *